(12) United States Patent
Abdallah et al.

(10) Patent No.: US 12,053,499 B1
(45) Date of Patent: Aug. 6, 2024

(54) SUSTAINABLE NANOCOMPOSITION FOR TREATMENT OF OSTEOPOROSIS

(71) Applicant: KING FAISAL UNIVERSITY, Al-Ahsa (SA)

(72) Inventors: Basem Mohamed Abdallah, Al-Ahsa (SA); Enas Mohamed Ali, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/429,310

(22) Filed: Jan. 31, 2024

(51) Int. Cl.
*A61K 36/00* (2006.01)
*A61K 36/899* (2006.01)
*A61K 45/06* (2006.01)
*A61K 47/69* (2017.01)

(52) U.S. Cl.
CPC ............ *A61K 36/899* (2013.01); *A61K 45/06* (2013.01); *A61K 47/6929* (2017.08); *A61K 2236/15* (2013.01); *A61K 2236/333* (2013.01)

(58) Field of Classification Search
CPC .......................... A61K 36/899; A61K 47/6929
See application file for complete search history.

(56) References Cited

FOREIGN PATENT DOCUMENTS

| CN | 116719667 A | 9/2023 |
|---|---|---|
| IN | 202241077024 | 1/2023 |
| KR | 10-2023-0105650 A | 7/2023 |

OTHER PUBLICATIONS

Chou et al., Phytotoxic substances in twelve subtropical grasses. J. Chem. Ecol, 1: 183-193, 1975.*

* cited by examiner

*Primary Examiner* — Qiuwen Mi
(74) *Attorney, Agent, or Firm* — Nath, Goldberg & Meyer; Joshua B. Goldberg

(57) ABSTRACT

A composition for treating osteoporosis comprising *Acroceras macrum* gold nanoparticles (AM-AuNPs). The composition is prepared by mixing an *Acroceras macrum* extract with an aqueous chloroauric acid ($HAuCl_4$) solution to provide a mixture including the *Acroceras macrum* gold nanoparticles; removing unreacted *Acroceras macrum* extract from the mixture followed by purifying the *Acroceras macrum* gold nanoparticles; and obtaining the gold nanoparticle composition comprising the *Acroceras macrum* gold nanoparticles (AM-AuNPs). The composition may be used to form drug compositions for treating osteoporosis.

20 Claims, 3 Drawing Sheets

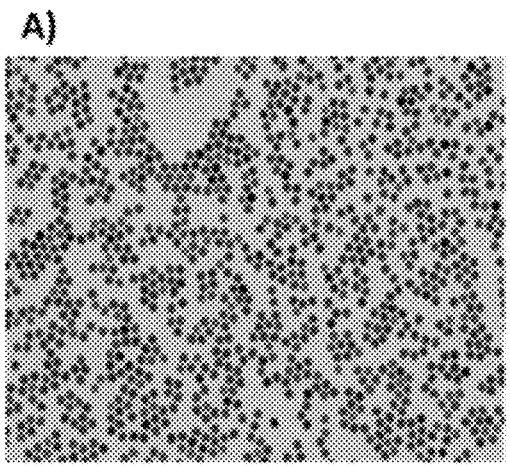 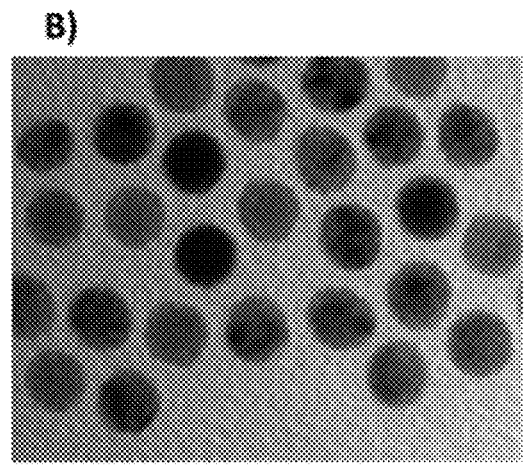
FIG. 3A  FIG. 3B
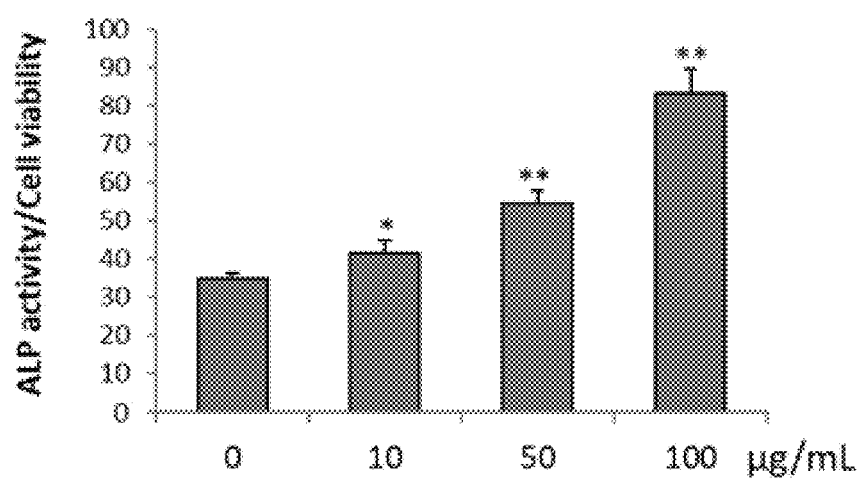
FIG. 4A

SUSTAINABLE NANOCOMPOSITION FOR TREATMENT OF OSTEOPOROSIS

BACKGROUND

1. Field

The disclosure of the present patent application relates to treating osteoporosis, and particularly to a composition for treating osteoporosis that includes a green composition of *Acroceras macrum*-derived gold nanoparticles (AM-AuNPs).

2. Description of the Related Art

Osteoporosis is a systemic bone loss-related disease that is characterized by reduced bone mass due to increase bone resorption by osteoclast cells on the expenses of bone formation by osteoblast cells. Accordingly, osteoporosis is a chronic disease resulting in an increased risk of bone fracture. The bone-forming progenitor osteoblast cells are derived from adult stem cells in bone marrow. Reduced osteoblast formation and activity is one of the main causes of osteoporosis.

Most drug therapy for osteoporosis is based mainly on inhibiting bone resorption (anti-catabolics), rather than enhancing bone formation. Thus, there is a need to develop new drug approach for targeting the stimulation of bone formation.

Nanoparticle-based approaches have been developed and widely used for stem cell regeneration therapy. However, most of these approaches use chemically synthesized nanoparticles to fabricate biocompatible and biodegradable nanoscaffolds/nanofibers for tissue engineering as bone graft alternatives, to use nanoparticles as a drug delivery system, to use nanoparticles for photo-thermal therapy of cancer, and for the formulation of quantum dots for labeling and imaging of the fate of implanted stem cells.

Thus, a composition for treating osteoporosis solving the aforementioned problems is desired.

SUMMARY

The present subject matter relates to use of a green composition of *Acroceras macrum*-derived gold nanoparticles (AM-AuNPs) for enhancing osteoblast differentiation, proliferation, and activity. Accordingly, the present compositions are effective for treating osteoporosis in a patient. The present AM-AuNPs can be used to enhance the differentiation of mesenchymal stem cells into osteoblast lineage and increase their matrix mineralization capacity in vitro and in vivo.

In an embodiment, the present subject matter relates to a gold nanoparticle composition, comprising *Acroceras macrum* gold nanoparticles (AM-AuNPs).

In another embodiment, the present subject matter relates to a composition for treating osteoporosis comprising the gold nanoparticle composition as described herein and a pharmaceutically acceptable carrier.

In an additional embodiment, the present subject matter relates to a method for treating osteoporosis in a patient, the method comprising administering to a patient in need thereof an effective amount of a composition as described herein for treating osteoporosis.

In a further embodiment, the present subject matter relates to a method for obtaining an *Acroceras macrum* extract, the method comprising: crushing aerial parts of an *Acroceras macrum* plant to obtain a fine powder; and extracting the fine powder in a solvent using a Soxhlet apparatus to obtain the *Acroceras macrum* extract.

In one more embodiment, the present subject matter relates to a method of synthesizing a gold nanoparticle composition, the method comprising: mixing the *Acroceras macrum* extract as described herein with an aqueous chloroauric acid ($HAuCl_4$) solution to provide a mixture including the *Acroceras macrum* gold nanoparticles; removing unreacted *Acroceras macrum* extract from the mixture followed by purifying the *Acroceras macrum* gold nanoparticles; and obtaining the gold nanoparticle composition comprising the *Acroceras macrum* gold nanoparticles (AM-AuNPs).

These and other features of the present subject matter will become readily apparent upon further review of the following specification and drawings.

BRIEF DESCRIPTION OF THE DRAWINGS

FIGS. 3A and 3B are (3A) a TEM image showing spherical morphology and physical diameter of the AuNPs; and (3B) a magnified view showing the conserved AuNPs size distribution.

FIGS. 4A and 4B are charts showing dose dependent stimulatory effects of the present AM-AuNPs on the osteoblas differentiation of BMSCs as measured by (4A) quantitative alkaline phosphatase activity (ALP); and (4B) Alizarin red staining after 6 days and 12 days of osteogenic induction, respectively.

Similar reference characters denote corresponding features consistently throughout the attached drawings.

DETAILED DESCRIPTION OF THE PREFERRED EMBODIMENTS

Figure 1:
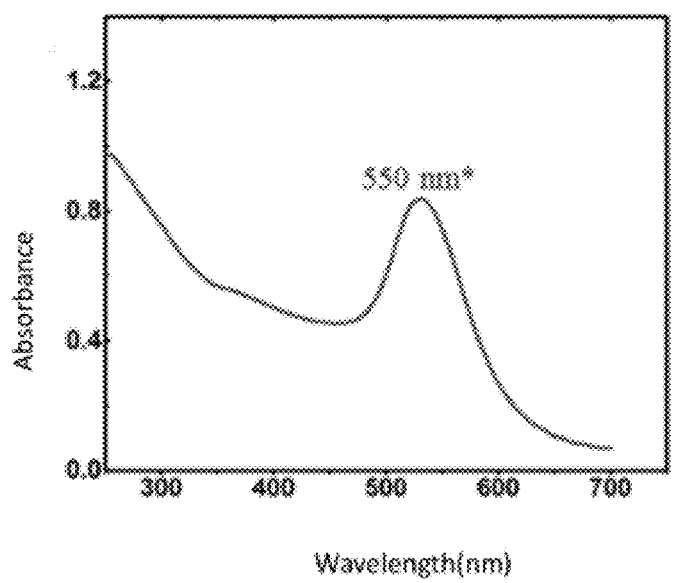
FIG. 1 is a chart showing the UV-Visible absorption spectra of the present gold nanoparticles.

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as bone loss or osteoporosis.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to use of a green composition of *Acroceras macrum*-dreved gold nanoparticles (AM-AuNPs) for enhancing osteoblast differentiation, proliferation, and activity. Accordingly, the present compositions are effective for treating osteoporosis in a patient. The present AM-AuNPs can be used to enhance the differentiation of mesenchymal stem cells into osteoblast lineage and increase their matrix mineralization capacity in vitro and in vivo.

In an embodiment, the present subject matter relates to a gold nanoparticle composition, comprising *Acroceras macrum* gold nanoparticles (AM-AuNPs).

In one embodiment, the *Acroceras macrum* gold nanoparticles can be obtained by a process comprising: providing an extract of *Acroceras macrum*; mixing the extract of *Acroceras macrum* with an aqueous chloroauric acid ($HAuCl_4$) solution to provide a mixture including the *Acroceras macrum* gold nanoparticles; removing unreacted *Acroceras macrum* extract from the mixture followed by purifying the *Acroceras macrum* gold nanoparticles; and obtaining the *Acroceras macrum* gold nanoparticles.

In this regard, in certain embodiments, the extract can be an extract of aerial parts of *Acroceras macrum*. Further, the extract of *Acroceras macrum* can be an extract in ethanol, methanol, or ethanol and methanol as extraction solvents.

In additional embodiments, the mixture can comprise about 1 mM of the aqueous chloroauric acid; and up to 100 μg/mL of the *Acroceras macrum* extract.

In another embodiment, the present subject matter relates to a composition for treating osteoporosis comprising the gold nanoparticle composition as described herein and a pharmaceutically acceptable carrier.

In certain embodiments, the composition for treating osteoporosis can further comprise one or more of α-cyperone, α-pinene, cyperotundone, and zierone.

In this regard, the present subject matter is further directed to pharmaceutical compositions comprising a therapeutically effective amount of the composition as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises a present composition together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present composition is typically administered at a therapeutically or pharmaceutically effective dosage, e.g., a dosage sufficient to provide treatment for osteoporosis or bone loss. Administration of the compound or pharmaceutical compositions thereof can be by any method that delivers the compound systemically and/or locally. These methods include oral routes and the like.

While human dosage levels have yet to be optimized for the present composition, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present composition for treatment of osteoporosis or bone loss, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols, or the like. The present compositions can also be administered in sustained or controlled release dosage forms, including osmotic pumps, pills, and the like, for the prolonged administration of the compound at a predetermined rate, preferably in unit dosage forms suitable for single administration of precise dosages.

The present compositions may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present composition, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum, and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

In an additional embodiment, the present subject matter relates to a method for treating osteoporosis in a patient, the method comprising administering to a patient in need thereof an effective amount of a composition as described herein for treating osteoporosis.

In certain embodiments, the present methods of treatment can include the reduction or reversal of bone loss. In other embodiments, the present treatment methods can further comprise stimulating differentiation of cells into osteoblasts in the patient, and/or enhancing osteoblast proliferation and activity in the patient.

In one embodiment, the composition can be orally administered to the patient. In this regard, about 50 mg of the composition can be orally administered to the patient once daily, for example, as a capsule.

In a further embodiment, the present subject matter relates to a method for obtaining an *Acroceras macrum* extract, the method comprising: crushing aerial parts of an *Acroceras macrum* plant to obtain a fine powder; and extracting the fine powder in a solvent using a Soxhlet apparatus to obtain the *Acroceras macrum* extract.

In certain embodiments, the present production methods can further comprise washing and air drying the aerial parts of the *Acroceras macrum* plant prior to the crushing step. Similarly, the extracting can be conducted for about four hours.

In another embodiment of the present production methods, the solvent can be ethanol, methanol, or a combination thereof.

In one more embodiment, the present subject matter relates to a method of synthesizing a gold nanoparticle composition, the method comprising: mixing the *Acroceras macrum* extract as described herein with an aqueous chloroauric acid ($HAuCl_4$) solution to provide a mixture including the *Acroceras macrum* gold nanoparticles; removing unreacted *Acroceras macrum* extract from the mixture followed by purifying the *Acroceras macrum* gold nanoparticles; and obtaining the gold nanoparticle composition comprising the *Acroceras macrum* gold nanoparticles (AM-AuNPs).

In certain embodiments of these methods, the removing unreacted *Acroceras macrum* extract from the mixture can be conducted by centrifugation. In this regard, the centrifugation can be conducted at about 3000 rpm to about 4000 rpm, or about 3500 rpm, and can be conducted for at least about 10 minutes, or about 10 minutes. In other embodiments, the purifying the *Acroceras macrum* gold nanoparticles can be conducted by centrifugation followed by washing with sterile distilled water. This second centrifugation step can be conducted at about 11,000 to about 13,000 rpm, or about 12,000 rpm, for at least about 20 minutes, or about 20 minutes.

In an embodiment, when making the mixture, the color of the mixture can change from pale yellow to vivid ruby-red, demonstrating the reduction of $AuCl_4$ and the formation of the AM-AuNPs.

The present disclosure can be further understood by referring to the following examples.

EXAMPLES

Example 1

Production of Extract of *Acroceras macrum*

The whole aerial parts of the *Acroceras macrum* plant were washed thoroughly with sterile distilled water, air dried, and then crushed into fine powder using a blender. 50 gm of powder were extracted with ethanol and methanol (300 mg/mL) using the Soxhlet apparatus for 4 hours. All of solvents were evaporated and then the extracts were dissolved in their solvent.

Example 2

Green Synthesis of AM-AuNPs 10 mL of the plant extract (100 mg/mL) was added to 60 mL of 1 mM aqueous $HAuCl_4$ solution. The change of color from pale yellow to vivid ruby-red demonstrates the reduction of $AuCl_4$ and the formation of AuNPs.

The suspension was centrifuged at 3500 rpm for 10 min to remove the unreacted plant extract. The biosynthesized nanoparticles were collected by centrifugation at 12,000 rpm for 20 min and purified by washing with sterile distilled water to obtain nanoparticles in pellet form. The purified AuNPs were then suspended in distilled water for further study.

FIG. 1 shows the UV-Visible absorption spectra of the present gold nanoparticles. The optical absorption spectra shows a surface plasmon resonance (SPR) of band at 550 nm, indicating it is in a metallic state.

Figure 2:
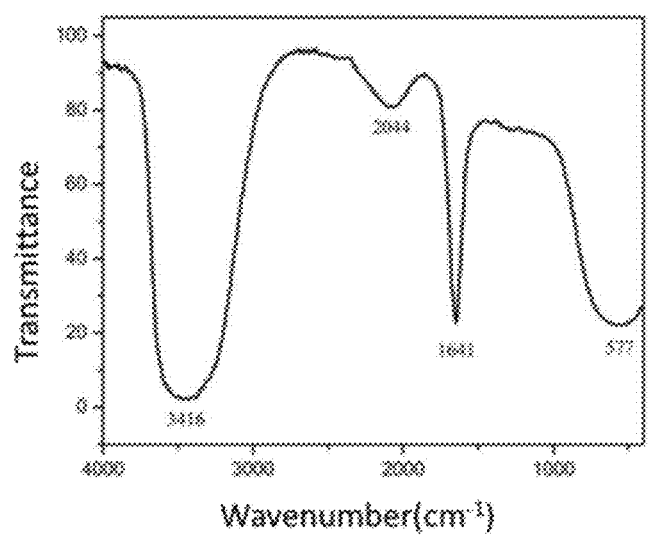
FIG. 2 is a chart showing the FTIR spectrum of the present AM-AuNPs gold nanoparticles.

FIG. 2 shows the FTIR spectrum of the present AM-AuNPs gold nanoparticles, which exhibits bands at 577, 1641, 2044, and 3416 $cm^{-1}$. The peak at 1641 $cm^{-1}$ was assigned to C—C stretching vibrations. The weak overtone band at 2044 $cm^{-1}$ indicated the presence of aromatic compounds on the nanoparticle surface, The peak at 3416 $cm^{-1}$ was assigned to O—H stretching vibrations which can be found in terpene and fatty acid extracts. The peak at 577 $cm^{-1}$ was attributed to C—Br stretching vibrations.

FIGS. 3A and 3B are (3A) a TEM image showing spherical morphology and physical diameter of the AuNPs; and (3B) a magnified view showing the conserved AuNPs size distribution.

Example 3

Stimulatory Effects of AM-AuNPs on Osteogenesis of Adult Bone Marrow-Derived Stem Cells (BSMCs)
Osteoblast Differentiation BMSCs were cultured at 15,000 cells/$cm^2$ in CIM medium. At 70% cell confluence, cultured media were changed to osteogenic-induction medium (OIM) consists of: α-minimum essential medium (α-MEM) containing 10% FBS, 100 U/mL of penicillin, 100 mg/mL of streptomycin, 50 μg/mL of vitamin C (Sigma-Aldrich), 10 nM dexamethasone and 10 mM β-glycerol-phosphate.

Figure 4B:
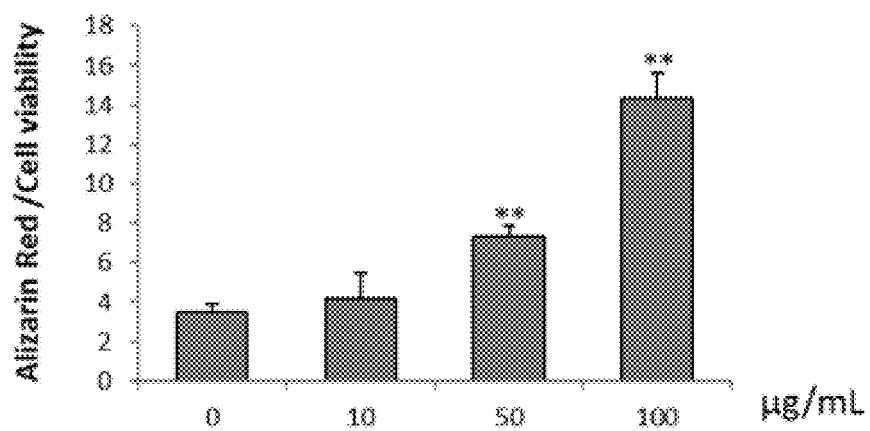

BMSCs were induced to differentiate into osteoblast as mentioned above in the absence or the presence of different concentrations of AM-AuNPs, for 12 days. As shown in FIG. 4, AM-AuNPs stimulated in dose-dependent manner the differentiation of BMSCs cells into osteoblast lineage, as measured by increasing the alkaline phosphatase activity and matrix mineralization using Alizarin red staining. The values in FIG. 4 are mean±SD of three independent experiments, (*$p<0.05$, **$p<0.005$, compared to non-treated cells).

It is to be understood that the composition for treating bone loss is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A gold nanoparticle composition, comprising *Acroceras macrum* gold nanoparticles (AM-AuNPs).
2. The gold nanoparticle composition of claim 1, wherein the *Acroceras macrum* gold nanoparticles are obtained by a process comprising:
   providing an extract of *Acroceras macrum*;
   mixing the extract of *Acroceras macrum* with an aqueous chloroauric acid ($HAuCl_4$) solution to provide a mixture including the *Acroceras macrum* gold nanoparticles;

removing unreacted *Acroceras macrum* extract from the mixture followed by purifying the *Acroceras macrum* gold nanoparticles; and obtaining the *Acroceras macrum* gold nanoparticles.

3. The gold nanoparticle composition of claim 2, wherein the extract is an extract of aerial parts of *Acroceras macrum*.

4. The gold nanoparticle composition of claim 2, wherein the extract of *Acroceras macrum* is an extract in ethanol and methanol as extraction solvents.

5. The gold nanoparticle composition of claim 2, wherein the mixture comprises:

about 1 mM of the aqueous chloroauric acid; and up to 100 µg/mL of the *Acroceras macrum* extract.

6. A composition for treating osteoporosis comprising the gold nanoparticle composition of claim 1 and a pharmaceutically acceptable carrier.

7. The composition for treating osteoporosis of claim 6, wherein the composition further comprises one or more of α-cyperone, α-pinene, cyperotundone, and zierone.

8. A method for treating osteoporosis in a patient, the method comprising administering to a patient in need thereof an effective amount of the composition of claim 1 for treating osteoporosis.

9. The method for treating osteoporosis in a patient of claim 8, wherein administering the compositions reduces or reverses bone loss.

10. The method for treating osteoporosis in a patient of claim 8, further comprising stimulating differentiation of cells into osteoblasts in the patient.

11. The method for treating osteoporosis in a patient of claim 8, further comprising enhancing osteoblast proliferation and activity in the patient.

12. The method for treating osteoporosis in a patient of claim 8, wherein the composition is orally administered to the patient.

13. The method for treating osteoporosis in a patient of claim 12, wherein about 50 mg of the composition is orally administered to the patient once daily.

14. A method for obtaining an *Acroceras macrum* extract, the method comprising:

crushing aerial parts of an *Acroceras macrum* plant to obtain a fine powder; and extracting the fine powder in a solvent using a Soxhlet apparatus to obtain the *Acroceras macrum* extract.

15. The method for obtaining the *Acroceras macrum* extract of claim 14, further comprising washing and air drying the aerial parts of the *Acroceras macrum* plant prior to the crushing step.

16. The method for obtaining the *Acroceras macrum* extract of claim 14, wherein the extracting is conducted for about four hours.

17. The method for obtaining the *Acroceras macrum* extract of claim 14, wherein the solvent is ethanol, methanol, or a combination thereof.

18. A method of synthesizing a gold nanoparticle composition, the method comprising:

mixing the *Acroceras macrum* extract obtained in claim 14 with an aqueous chloroauric acid ($HAuCl_4$) solution to provide a mixture including the *Acroceras macrum* gold nanoparticles;

removing unreacted *Acroceras macrum* extract from the mixture followed by purifying the *Acroceras macrum* gold nanoparticles; and obtaining the gold nanoparticle composition comprising the *Acroceras macrum* gold nanoparticles (AM-AuNPs).

19. The method of synthesizing a gold nanoparticle composition of claim 18, wherein the removing unreacted *Acroceras macrum* extract from the mixture is conducted by centrifugation.

20. The method of synthesizing a gold nanoparticle composition of claim 18, wherein the purifying the *Acroceras macrum* gold nanoparticles is conducted by centrifugation followed by washing with sterile distilled water.

* * * * *